US009689778B2

(12) United States Patent
Sun et al.

(10) Patent No.: US 9,689,778 B2
(45) Date of Patent: Jun. 27, 2017

(54) METHOD OF ESTIMATING SOOT OUTPUT FROM AN ENGINE

(71) Applicant: GM GLOBAL TECHNOLOGY OPERATIONS LLC, Detroit, MI (US)

(72) Inventors: Min Sun, Troy, MI (US); Michelangelo Ardanese, Royal Oak, MI (US); Michele Bilancia, Turin (IT); Giorgio Sticchi, Maglie (IT)

(73) Assignee: GM Global Technology Operations LLC, Detroit, MI (US)

( * ) Notice: Subject to any disclaimer, the term of this patent is extended or adjusted under 35 U.S.C. 154(b) by 648 days.

(21) Appl. No.: 14/168,485

(22) Filed: Jan. 30, 2014

(65) Prior Publication Data

US 2015/0211962 A1    Jul. 30, 2015

(51) Int. Cl.
*G01M 15/10*    (2006.01)
*G01N 33/00*    (2006.01)

(52) U.S. Cl.
CPC ...... *G01M 15/102* (2013.01); *G01N 33/0036* (2013.01)

(58) Field of Classification Search
CPC ..... G01M 15/102; G01M 15/00–15/12; G01N 33/0036
See application file for complete search history.

(56) References Cited

U.S. PATENT DOCUMENTS

| | | | |
|---|---|---|---|
| 7,562,524 B2* | 7/2009 | Wills | F01N 3/0231 60/286 |
| 2011/0209460 A1* | 9/2011 | He | F01N 9/002 60/274 |
| 2012/0216507 A1* | 8/2012 | Nieuwstadt | F01N 3/101 60/274 |
| 2014/0338434 A1* | 11/2014 | Sun | F02D 41/1448 73/114.75 |

* cited by examiner

*Primary Examiner* — Mohamed Charioui
*Assistant Examiner* — Jeremy Delozier
(74) *Attorney, Agent, or Firm* — Quinn IP Law

(57) ABSTRACT

A method of estimating a current soot output from an engine includes sensing a mass flow rate of a flow of exhaust gas from the engine, and defining a soot output base rate of the engine when the engine is operating at a reference state. A soot ratio for a current operating state of the engine is calculated. The mass flow rate, the soot output base rate, and the soot ratio are multiplied together to define an estimated value of the current soot output from the engine. The soot ratio is based on current engine operating parameters, including an air/fuel ratio of the engine, an exhaust gas recirculation ratio of the engine, a fuel injection pressure of the engine, and a fuel injection timing of the engine.

18 Claims, 3 Drawing Sheets

METHOD OF ESTIMATING SOOT OUTPUT FROM AN ENGINE

TECHNICAL FIELD

The invention generally relates to a method of estimating a current soot output from an engine.

BACKGROUND

Vehicles include an exhaust gas treatment system for treating a flow of exhaust gas from an engine. The exhaust gas treatment system may include one or more structures that collect soot therein, such as but not limited to, a particulate filter. When the engine includes a diesel engine, the particulate filter is often referred to as a diesel particulate filter. The amount of soot that the engine produces varies as the operating states of the engine change, e.g., the engine may produce more soot when operating under a heavy load, then when operating under a light load. In order to properly control and/or monitor the exhaust gas treatment system, the vehicle must estimate the amount of soot that the engine produces. For example, the exhaust gas treatment system may include a soot sensor disposed downstream of the particulate filter. The soot sensor senses the amount of soot remaining in the flow of exhaust gas downstream from the particulate filter. However, in order to determine if the particulate filter is functioning properly, the vehicle must estimate how much soot is being introduced into the flow of exhaust gas from the engine, upstream of the particulate filter, to be able to determine an acceptable level of soot in the flow of exhaust gas downstream of the particulate filter. The estimated amount of soot produced by the engine may also be used to determine when to initiate regeneration of the particulate filter.

SUMMARY

A method of estimating a current soot output from an engine is provided. The method includes sensing a mass flow rate of a flow of exhaust gas from the engine, and defining a soot output base rate of the engine when the engine is operating at a reference state. A soot ratio for a current operating state of the engine is calculated. The mass flow rate, the soot output base rate, and the soot ratio are multiplied together to define an estimated value of the current soot output from the engine.

Accordingly, the product of the mass flow rate and the soot output base rate provides an estimate of how much soot the engine produces at a reference operating state, such as a steady state test condition. The soot ratio is a multiplier that adjusts this product to account for the current operating states of the engine. Accordingly, multiplying the product of the mass flow rate and the soot output base rate by the soot ratio provides an estimate for the amount of soot output from the engine at the current operating states.

The above features and advantages and other features and advantages of the present invention are readily apparent from the following detailed description of the best modes for carrying out the invention when taken in connection with the accompanying drawings.

DETAILED DESCRIPTION

Those having ordinary skill in the art will recognize that terms such as "above," "below," "upward," "downward," "top," "bottom," etc., are used descriptively for the figures, and do not represent limitations on the scope of the invention, as defined by the appended claims. Furthermore, the invention may be described herein in terms of functional and/or logical block components and/or various processing steps. It should be realized that such block components may be comprised of any number of hardware, software, and/or firmware components configured to perform the specified functions.

Figure 1:
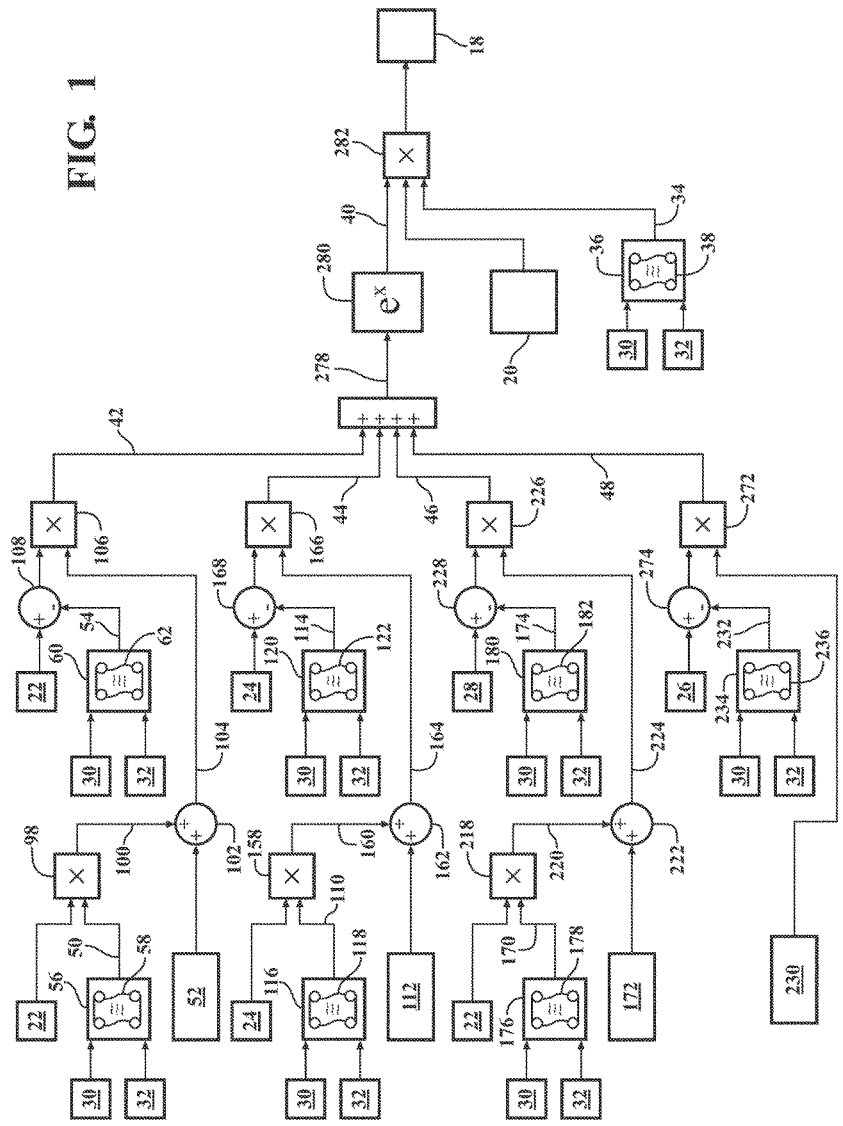
FIG. 1 is schematic diagram showing a mapping structure for estimating the soot output from an engine.

Referring to the Figures, wherein like numerals indicate like parts throughout the several views, a mapping structure/flowchart showing a method of estimating a current soot output from an engine is generally shown in FIG. 1. The method is used to estimate a current soot output 18 of the engine, such as but not limited to, a diesel engine, at a current operating state. The current soot output 18 at the current operating state may be tracked over time to estimate the total amount of soot produced by the engine during that period of time.

The current operating state of the engine encompasses various different operating parameters of the engine at any given time. As such, the current operating state of the engine changes over time as the different operating parameters of the engine are changed. The different operating parameters of the engine that may be adjusted to change the current operating state of the engine include, but are not limited to, a rotational speed 30 of the engine, a fuel injection rate 32 of the engine, a fuel injection pressure 28 of the engine, a fuel injection timing 26 of the engine, an air/fuel ratio 22 of the engine, and an exhaust gas recirculation rate 24 of the engine.

The rotational speed 30 of the engine may be defined as the rotational speed 30 at which a crankshaft of the engine rotates. The fuel injection rate 32 of the engine may be defined as the quantity of fuel injected into the engine during a specified period of time. The fuel injection pressure 28 of the engine may be defined as the pressure (e.g., psi) of the fuel when injected into the engine for combustion. The fuel injection timing 26 of the engine may be defined as the position of a piston during a piston stroke at which the fuel is injected into a respective cylinder of the piston. The air/fuel ratio 22 of the engine may be defined as the amount of fuel mixed with a pre-defined quantity of air, which is injected into the cylinders of the engine. The exhaust gas recirculation rate 24 may be defined as the amount or percentage of exhaust gas that is recirculated into the intake air of the engine for injection into the cylinders of the engine for combustion.

The vehicle may include a controller to control and/or monitor the operation of the engine and/or an exhaust gas treatment system of the engine. The controller may include a computer and/or processor, and include all software, hardware, memory, algorithms, connections, sensors, etc., necessary to manage, monitor, and control the operation of the engine and the exhaust gas treatment system. As such, the method described below may be embodied as a program operable on the controller. It should be appreciated that the controller may include any device capable of analyzing data from various sensors, comparing data, making the necessary decisions required to control the operation of the engine and/or exhaust gas treatment system, and perform the various calculations required to calculate the current soot output 18 from the engine.

Referring to FIG. 1, the method includes sensing a mass flow rate of the flow of exhaust gas from the engine, generally indicated by box 20. The mass flow rate 20 of the exhaust gas is the mass of exhaust gas that passes through the exhaust gas treatment system of the engine per unit of time. The mass flow rate 20 of the exhaust gas may be sensed in any suitable manner.

The method may further include sensing and/or otherwise determining the various operating parameters of the engine at the current operating state of the engine. Specifically, the method may include sensing and/or determining the air/fuel ratio 22 of the engine at the current operating state, sensing and/or determining the exhaust gas recirculation rate 24 of the engine at the current operating state, sensing and/or determining the fuel injection timing 26 of the engine at the current operating state, sensing and/or determining the fuel injection pressure 28 of the engine at the current operating state, sensing and/or determining the rotational speed 30 of the engine at the current operating state, and sensing and/or determining the fueling rate 32 of the engine at the current operating state.

A soot output base rate 34 of the engine is defined for when the engine is operating at a reference state. The reference state may be any specific operating state of the engine, but is typically defined as a steady state operating state at defined operating parameters. For example, the reference state may include an engine idle condition with all of the various operating parameters of the engine set at a pre-defined limit/rate. The soot output base rate 34 is the amount of soot that the engine produces per unit time while the engine is operating at the reference state.

As shown in FIG. 1, defining the soot output base rate 34 of the engine, generally indicated by box 36, for when the engine is operating at the reference state, may include referencing a base soot table 38 stored in the memory of the controller. The base soot table 38 may be defined as a two dimensional table, that uses two input values to define an output value. The soot output base rate 34 of the engine at the reference state is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the base soot table 38, to look-up and/or define the value for the soot output base rate 34 of the engine at the reference state, which is the output of the base soot table 38.

Referring to FIG. 1, a soot ratio 40 for the current operating state of the engine is calculated. The manner in which the soot ratio 40 is calculated is described in detail below. The mass flow rate 20, the soot output base rate 34, and the soot ratio 40 are then multiplied together to define an estimated value of the current soot output 18 from the engine. Accordingly, the estimated value of the current soot output 18 of the engine is calculated from Equation 1:

$$\text{sootoutput} = (M_{exh})(\text{Soot}_{base})(\text{sootratio}); \qquad 1)$$

wherein the sootoutput is the current soot output 18 of the engine at the current operating states, $M_{exh}$ is the mass flow rate 20 of exhaust gas at the current operating state of the engine, $\text{Soot}_{base}$ is the soot output base rate 34 of the engine when operating at the reference state, and sootratio is the soot ratio 40 for the current operating state of the engine.

The soot ratio 40 relates the amount of soot produced by the engine at the current operating state to the amount of soot produced by the engine at the reference state. The soot ratio 40 of the engine is calculated from Equation 2:

$$\text{sootratio} = e^{((AFRpor)+(EGRpor)+(InjPpor)+(InjTpor))}; \qquad 2)$$

wherein e is the base of the natural logarithm, and is the mathematical constant often referred to as Euler's Number, AFRpor is an air/fuel ratio portion 42 of the soot ratio 40, EGRpor is an exhaust gas recirculation portion 44 of the soot ratio 40, InjPpor is a fuel injection pressure portion 46 of the soot ratio 40, and InjTpor is a fuel injection timing portion 48 of the soot ratio 40.

The air/fuel ratio portion 42 (AFRpor) is calculated from Equation 3:

$$\text{AFRpor} = [(a_{AFR})(\text{AFR}) + (f_{AFR})][\text{AFR} - (\text{AFR}_{base})]; \qquad 3)$$

wherein AFR is the air/fuel ratio 22 of the engine at the current operating state, $a_{AFR}$ is an AFR term coefficient 50 for the air/fuel ratio 22, $f_{AFR}$ is a functional timing value 52 of the air/fuel ratio 22, and $\text{AFR}_{base}$ is an air/fuel ratio base value 54 of the engine when the engine is operating at the reference state.

The AFR term coefficient 50 is a function of the rotational speed 30 of the engine and the fueling rate 32 of the engine. The AFR term coefficient 50 is a constant for any given combination of the rotational speed 30 and the fueling rate 32 of the engine. The AFR term coefficient 50 is determined from test data generated for each combination of the rotational speed 30 and the fueling rate 32 of the specific engine being used.

As shown in FIG. 1, defining and/or determining the AFR term coefficient 50 ($a_{AFR}$), generally indicated by box 56, which is used to calculate the air/fuel ratio portion 42 of the soot ratio 40, may include referencing an AFR term table 58 stored in the memory of the controller. The AFR term table 58 may be defined as a two dimensional table, that uses two input values to define an output value. The AFR term coefficient 50 used to calculate the air/fuel ratio portion 42 of the soot ratio 40 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the AFR term table 58, to look-up and/or define the value for the AFR term coefficient 50 used to calculate the air/fuel ratio portion 42 of the soot ratio 40, which is the output of the AFR term table 58.

The air/fuel ratio base value 54 ($\text{AFR}_{base}$) is the air/fuel ratio 22 of the engine when the engine is operating at the reference state. As shown in FIG. 1, defining and/or determining the air/fuel ratio base value 54 ($\text{AFR}_{base}$) generally indicated by box 60, which is used to calculate the air/fuel ratio portion 42 of the soot ratio 40, may include referencing an AFR base table 62 stored in the memory of the controller. The AFR base table 62 may be defined as a two dimensional table, that uses two input values to define an output value.

The air/fuel ratio base value 54 used to calculate the air/fuel ratio portion 42 of the soot ratio 40 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the AFR base table 62, to look-up and/or define the value for the air/fuel ratio base value 54 used to calculate the air/fuel ratio portion 42 of the soot ratio 40, which is the output of the AFR base table 62.

The functional timing value 52 ($f_{AFR}$) of the air/fuel ratio 22 is determined based upon the rotational speed 30 of the engine at the current operating state, the fueling rate 32 of the engine at the current operating state, and the fuel injection timing 26 of the engine at the current operating state. The functional timing value 52 of the air/fuel ratio 22 is determined or calculated from Equation 4)

$$f_{AFR} = b_2(f((b_1)(InjT))) + b_3; \qquad 4)$$

wherein $b_1$ is a coefficient 64 for the functional timing value 52 of the air/fuel ratio 22, $b_2$ is a coefficient 66 of the fuel injection timing 26 of the engine, $b_3$ is an adjustment value 68 of the functional timing value 52 of the air/fuel ratio 22, and InjT is the fuel injection timing 26 of the engine at the current operating state of the engine. The functional timing value 52 ($f_{AFR}$) of the air/fuel ratio 22 is determined and/or calculated from the coefficient 64 for the functional timing value 52 of the air fuel ratio 22, the coefficient 66 of the fuel injection timing 26 of the engine, and the adjustment value 68 of the functional timing value 52 of the air/fuel ratio 22.

Figure 2:
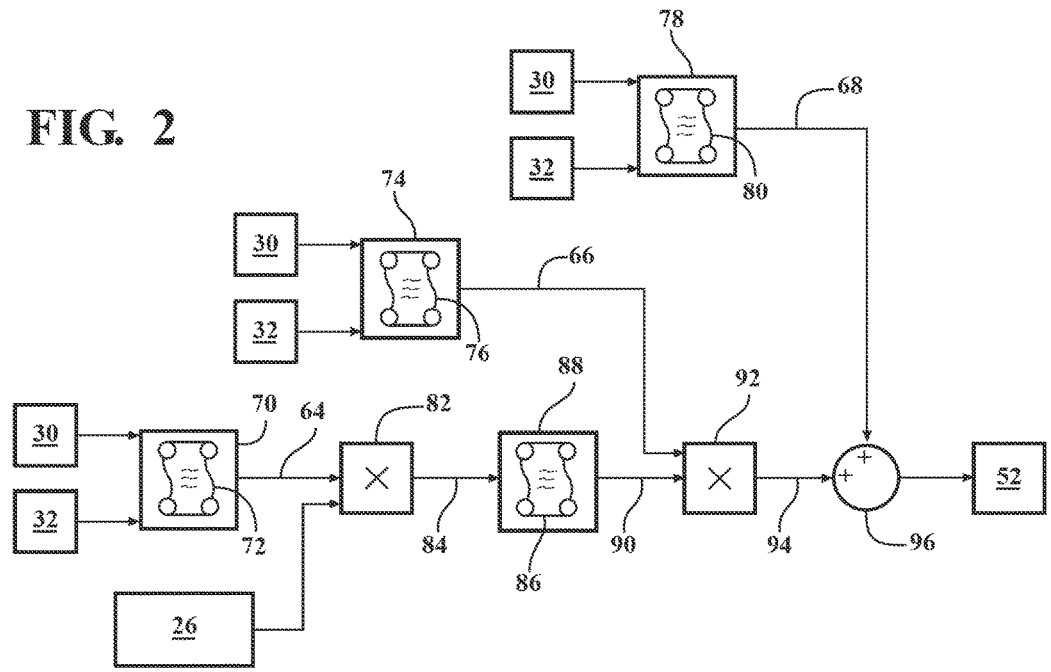
FIG. 2 is a schematic diagram showing a mapping structure for determining a functional timing value of an air/fuel ratio of the engine.

Referring to FIG. 2, the coefficient 64 ($b_1$) for the functional timing value 52 of the air/fuel ratio 22 is determined and/or defined, generally indicated by box 70, by referencing an AFR-B1 input table 72 stored in the memory of the controller. The AFR-B1 input table 72 may be defined as a two dimensional table, that uses two input values to define an output value. The coefficient 64 ($b_1$) for the functional timing value 52 of the air/fuel ratio 22 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the AFR-B1 input table 72, to look-up and/or define the value for the coefficient 64 ($b_1$) for the functional timing value 52 of the air/fuel ratio 22, which is the output of the AFR-B1 input table 72.

Coefficient 64 is a function of the rotational speed 30 of the engine and the fueling rate 32 of the engine. Coefficient 64 is a constant for any given combination of the rotational speed 30 and the fueling rate 32 of the engine. Coefficient 64 is determined from test data generated for each combination of the rotational speed 30 and the fueling rate 32 of the specific engine being used.

As shown in FIG. 2, the coefficient 66 ($b_2$) for the functional timing value 52 of the air/fuel ratio 22 is determined and/or defined, generally indicated by box 74, by referencing an AFR-B2 multiplier table 76 stored in the memory of the controller. The AFR-B2 multiplier table 76 may be defined as a two dimensional table, that uses two input values to define an output value. The coefficient 66 ($b_2$) for the functional timing value 52 of the air/fuel ratio 22 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the AFR-B2 multiplier table 76, to look-up and/or define the value for the coefficient 66 ($b_2$) for the functional timing value 52 of the air/fuel ratio 22, which is the output of the AFR-B2 multiplier table 76.

Coefficient 66 is a function of the rotational speed 30 of the engine and the fueling rate 32 of the engine. Coefficient 66 is a constant for any given combination of the rotational speed 30 and the fueling rate 32 of the engine. Coefficient 66 is determined from test data generated for each combination of the rotational speed 30 and the fueling rate 32 of the specific engine being used.

As shown in FIG. 2, the adjustment value 68 ($b_3$) for the functional timing value 52 of the air/fuel ratio 22 is determined and/or defined, generally indicated by box 78, by referencing an AFR-B3 adjustment table 80 stored in the memory of the controller. The AFR-B3 adjustment table 80 may be defined as a two dimensional table, that uses two input values to define an output value. The adjustment value 68 ($b_3$) for the functional timing value 52 of the air/fuel ratio 22 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the AFR-B3 adjustment table 80, to look-up and/or define the value for the adjustment value 68 ($b_3$) for the functional timing value 52 of the air/fuel ratio 22, which is the output of the AFR-B3 adjustment table 80.

The adjustment value 68 is a function of the rotational speed 30 of the engine and the fueling rate 32 of the engine. The adjustment value 68 is a constant for any given combination of the rotational speed 30 and the fueling rate 32 of the engine. The adjustment value 68 is determined from test data generated for each combination of the rotational speed 30 and the fueling rate 32 of the specific engine being used.

As shown in FIG. 2, the fuel injection timing 26 (InjT) of the engine at the current operating state is multiplied, generally indicated by box 82, by the coefficient 64 ($b_1$) for the functional timing value 52 of the air/fuel ratio 22, which is the output of the AFR-B1 input table 72. The product 84 of the fuel injection timing 26 and the coefficient 64 ($b_1$) for the functional timing value 52 of the air/fuel ratio 22 is used as an input into an AFR calibration table 86. The AFR calibration table 86 is a one dimensional table that uses a single input to define a single output value. Accordingly, the output value of the AFR calibration table 86 defines the value of the function $f((b_1)(InjT))$. As such, the function $f((b_1)(InjT))$ is determined, generally indicated by box 88, from the AFR calibration table 86 based upon the product 84 of the coefficient 64 ($b_1$) for the functional timing value 52 of the air/fuel ratio 22 and the fuel injection timing 26 of the engine at the current operating state. Accordingly, the controller may use the product 84 of the coefficient 64 ($b_1$) for the functional timing value 52 of the air/fuel ratio 22 and the fuel injection timing 26 of the engine at the current operating state as the single input into the AFR calibration table 86, to look-up and/or define the value for the function $f((b_1)(InjT))$, which is the output 90 of the AFR calibration table 86.

The AFR calibration table 86 is universal for the rotational speed 30 and the fuel rate 32 of the engine. The AFR calibration table 86 is developed by adjusting the values of the table 86 to achieve the best soot rate estimation at all engine speeds and fueling rate conditions.

As shown in FIG. 2, the value for the function $f((b_1)(InjT))$, which is the output 90 of the AFR calibration table 86, is multiplied, generally indicated by box 92, by the value for the coefficient 66 ($b_2$) for the functional timing value 52 of the air/fuel ratio 22, which is the output of the AFR-B2 multiplier table 76. The product 94 of the function $f((b_1)(InjT))$ and the coefficient 66 ($b_2$) for the functional timing value 52 of the air/fuel ratio 22 is then added, generally indicated by box 96, to the adjustment value 68 ($b_3$) for the functional timing value 52 of the air/fuel ratio 22, which is the output of the AFR-B3 adjustment table 80, to define and/or calculate the functional timing value 52 ($f_{AFR}$) of the air/fuel ratio 22.

Referring back to FIG. 1, the air/fuel ratio 22 (AFR) of the engine at the current operating state is multiplied, generally indicated by box 98, by the AFR term coefficient 50 used to calculate the air/fuel ratio portion 42 of the soot ratio 40, which is the output of the AFR term table 58. The product 100 of the air/fuel ratio 22 (AFR) of the engine at the current operating state and the AFR term coefficient 50 used to calculate the air/fuel ratio portion 42 of the soot ratio 40 is added, generally indicated by box 102, to the functional timing value 52 ($f_{AFR}$) of the air/fuel ratio 22, to define an AFR portion sum 104. The AFR portion sum 104 is then multiplied, generally indicated by box 106, by the difference, generally indicated by box 108, between the air/fuel ratio 22 (AFR) of the engine at the current operating state and the air/fuel ratio base value 54 (AFR$_{base}$) used to calculate the air/fuel ratio portion 42 of the soot ratio 40, to calculate the air/fuel ratio portion 42 (AFRpor) of the current soot output 18.

The exhaust gas recirculation portion 44 (EGRpor) is calculated from Equation 5:

$$\text{EGRpor}=[(a_{EGR})(\text{EGR})+(f_{EGR})][(\text{EFR})-(\text{EGR}_{base})]; \qquad 5)$$

wherein EGR is the exhaust gas recirculation ratio 24 of the engine at the current operating state, $a_{EGR}$ is an EGR term coefficient 110 for the exhaust gas recirculation ratio 24, $f_{EGR}$ is a functional timing value 112 of the exhaust gas recirculation ratio 24, and EGR$_{base}$ is an exhaust gas recirculation base rate 114 of the engine when the engine is operating at the reference state;

The EGR term coefficient 110 is a function of the rotational speed 30 of the engine and the fueling rate 32 of the engine. The EGR term Coefficient 110 is a constant for any given combination of the rotational speed 30 and the fueling rate 32 of the engine. The EGR term coefficient 110 is determined from test data generated for each combination of the rotational speed 30 and the fueling rate 32 of the specific engine being used.

Referring to FIG. 1, defining and/or determining the EGR term coefficient 110 ($a_{EGR}$), generally indicated by box 116, which is used to calculate the exhaust gas recirculation portion 44 of the soot ratio 40, may include referencing an EGR term table 118 stored in the memory of the controller. The EGR term table 118 may be defined as a two dimensional table, that uses two input values to define an output value. The EGR term coefficient 110 used to calculate the exhaust gas recirculation portion 44 of the soot ratio 40 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the EGR term table 118, to look-up and/or define the value for the EGR term coefficient 110 used to calculate the exhaust gas recirculation portion 44 of the soot ratio 40, which is the output of the EGR term table 118.

The exhaust gas recirculation base ratio 114 (EGR$_{base}$) is the exhaust gas recirculation ratio 24 of the engine when the engine is operating at the reference state. As shown in FIG. 1, defining and/or determining the exhaust gas recirculation base ratio 114 (EGR$_{base}$) generally indicated by box 120, which is used to calculate the exhaust gas recirculation portion 44 of the soot ratio 40, may include referencing an EGR base table 122 stored in the memory of the controller. The EGR base table 122 may be defined as a two dimensional table, that uses two input values to define an output value. The exhaust gas recirculation base ratio 114 used to calculate the exhaust gas recirculation portion 44 of the soot ratio 40 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the EGR base table 122, to look-up and/or define the value for the exhaust gas recirculation base ratio 114 used to calculate the exhaust gas recirculation portion 44 of the soot ratio 40, which is the output of the EGR base table 122.

The functional timing value 112 ($f_{EGR}$) of the exhaust gas recirculation ratio 24 is determined based upon the rotational speed 30 of the engine at the current operating state, the fueling rate 32 of the engine at the current operating state, and the fuel injection timing 26 of the engine at the current operating state. The functional timing value 112 of the exhaust gas recirculation ratio 24 is determined or calculated from Equation 6)

$$f_{EGR}=b_2(f((b_1)(\text{Inj}T)))+b_3; \qquad 6)$$

wherein $b_1$ is a coefficient 124 for the functional timing value 112 of the exhaust gas recirculation ratio 24, $b_2$ is a coefficient 126 of the fuel injection timing 26 of the engine, $b_3$ is an adjustment value 128 of the functional timing value 112 of the exhaust gas recirculation ratio 24, and InjT is the fuel injection timing 26 of the engine at the current operating state of the engine. The functional timing value 112 ($f_{EGR}$) of the exhaust gas recirculation ratio 24 is determined and/or calculated from the coefficient 124 for the functional timing value 112 of the exhaust gas recirculation ratio 24, the coefficient 126 of the fuel injection timing 26 of the engine, and the adjustment value 128 of the functional timing value 112 of the exhaust gas recirculation ratio 24.

Figure 3:
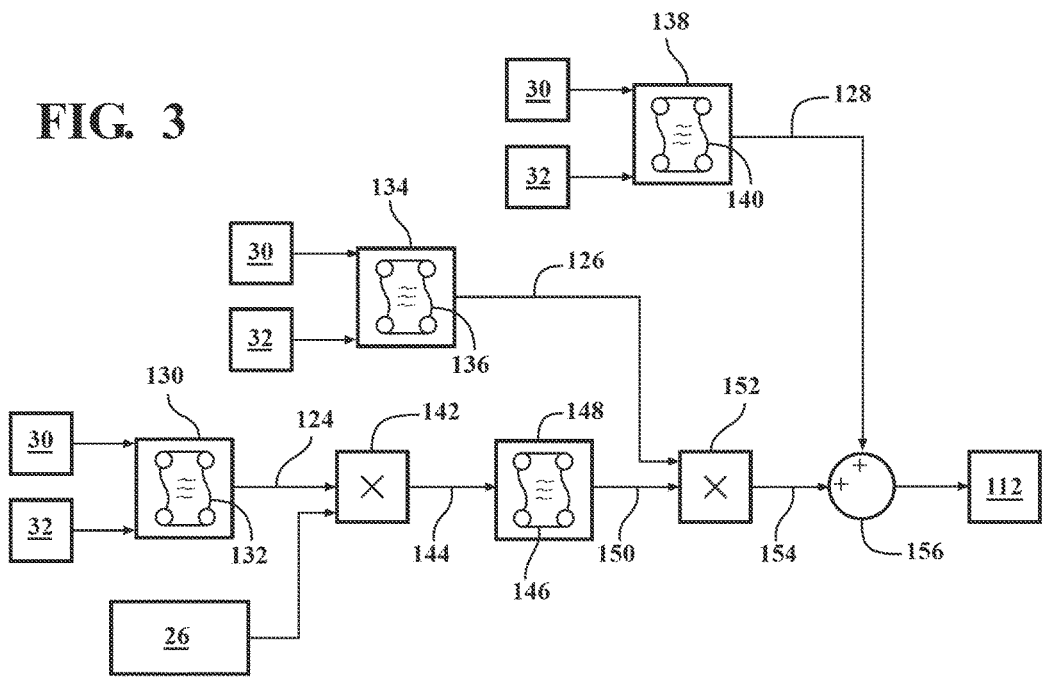
FIG. 3 is a schematic diagram showing a mapping structure for determining a functional timing value of an exhaust gas recirculation rate of the engine.

Referring to FIG. 3, the coefficient 124 ($b_1$) for the functional timing value 112 of the exhaust gas recirculation ratio 24 is determined and/or defined, generally indicated by box 130, by referencing an EGR-B1 input table 132 stored in the memory of the controller. The EGR-B1 input table 132 may be defined as a two dimensional table, that uses two input values to define an output value. The coefficient 124 ($b_1$) for the functional timing value 112 of the exhaust gas recirculation ratio 24 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the EGR-B1 input table 132, to look-up and/or define the value for the coefficient 124 ($b_1$) for the functional timing value 112 of the exhaust gas recirculation ratio 24, which is the output of the EGR-B1 input table 132.

The coefficient 124 is a function of the rotational speed 30 of the engine and the fueling rate 32 of the engine. The coefficient 124 is a constant for any given combination of the rotational speed 30 and the fueling rate 32 of the engine. The coefficient 124 is determined from test data generated for each combination of the rotational speed 30 and the fueling rate 32 of the specific engine being used.

As shown in FIG. 3, the coefficient 126 ($b_2$) for the functional timing value 112 of the exhaust gas recirculation ratio 24 is determined and/or defined, generally indicated by box 134, by referencing an EGR-B2 multiplier table 136 stored in the memory of the controller. The EGR-B2 multiplier table 136 may be defined as a two dimensional table, that uses two input values to define an output value. The coefficient 126 ($b_2$) for the functional timing value 112 of the exhaust gas recirculation ratio 24 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the EGR-B2 multiplier table 136, to look-up and/or define the value for the coefficient 126 ($b_2$) for the functional timing value 112 of the exhaust gas recirculation ratio 24, which is the output of the EGR-B2 multiplier table 136.

The coefficient 126 is a function of the rotational speed 30 of the engine and the fueling rate 32 of the engine. The coefficient 126 is a constant for any given combination of the rotational speed 30 and the fueling rate 32 of the engine. The coefficient 126 is determined from test data generated for each combination of the rotational speed 30 and the fueling rate 32 of the specific engine being used.

As shown in FIG. 3, the adjustment value 128 ($b_3$) for the functional timing value 112 of the exhaust gas recirculation ratio 24 is determined and/or defined, generally indicated by box 138, by referencing an EGR-B3 adjustment table 140 stored in the memory of the controller. The EGR-B3 adjustment table 140 may be defined as a two dimensional table, that uses two input values to define an output value. The adjustment value 128 ($b_3$) for the functional timing value 112 of the exhaust gas recirculation ratio 24 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the EGR-B3 adjustment table 140, to look-up and/or define the value for the adjustment value 128 ($b_3$) for the functional timing value 112 of the exhaust gas recirculation ratio 24, which is the output of the EGR-B3 adjustment table 140.

The adjustment value 128 is a function of the rotational speed 30 of the engine and the fueling rate 32 of the engine. The adjustment value 128 is a constant for any given combination of the rotational speed 30 and the fueling rate 32 of the engine. The adjustment value 128 is determined from test data generated for each combination of the rotational speed 30 and the fueling rate 32 of the specific engine being used.

As shown in FIG. 3, the fuel injection timing 26 (InjT) of the engine at the current operating state is multiplied, generally indicated by box 142, by the coefficient 124 ($b_1$) for the functional timing value 112 of the exhaust gas recirculation ratio 24, which is the output of the EGR-B1 input table 132. The product 144 of the fuel injection timing 26 and the coefficient 124 ($b_1$) for the functional timing value 112 of the exhaust gas recirculation ratio 24 is used as an input into an EGR calibration table 146. The EGR calibration table 146 is a one dimensional table that uses a single input to define a single output value. Accordingly, the output value of the EGR calibration table 146 defines the value of the function $f((b_1)(InjT))$. As such, the function $f((b_1)(InjT))$ is determined, generally indicated by box 148, from the EGR calibration table 146 based upon the product 144 of the coefficient 124 ($b_1$) for the functional timing value 112 of the exhaust gas recirculation ratio 24 and the fuel injection timing 26 of the engine at the current operating state. Accordingly, the controller may use the product 144 of the coefficient 124 ($b_1$) for the functional timing value 112 of the exhaust gas recirculation ratio 24 and the fuel injection timing 26 of the engine at the current operating state as the single input into the EGR calibration table 146, to look-up and/or define the value for the function $f((b_1)(InjT))$, which is the output 150 of the EGR calibration table 146.

The EGR calibration table 146 is universal for the rotational speed 30 and the fuel rate 32 of the engine. The EGR calibration table 146 is developed by adjusting the values of the table 146 to achieve the best soot rate estimation at all engine speeds and fueling rate conditions.

As shown in FIG. 3, the value for the function $f((b_1)(InjT))$, which is the output 150 of the EGR calibration table 146, is multiplied, generally indicated by box 152, by the value of the coefficient 126 ($b_2$) for the functional timing value 112 of the exhaust gas recirculation ratio 24, which is the output of the EGR-B2 multiplier table 136. The product 154 of the function $f((b_1)(InjT))$ and the coefficient 126 ($b_2$) for the functional timing value 112 of the exhaust gas recirculation ratio 24 is then added, generally indicated by box 156, to the adjustment value 128 ($b_3$) for the functional timing value 112 of the exhaust gas recirculation ratio 24, which is the output of the EGR-B3 adjustment table 140, to define and/or calculate the functional timing value 112 ($f_{EGR}$) of the exhaust gas recirculation ratio 24.

Referring back to FIG. 1, the exhaust gas recirculation ratio 24 (EGR) of the engine at the current operating state is multiplied, generally indicated by box 158, by the EGR term coefficient 110 used to calculate the exhaust gas recirculation portion 44 of the soot ratio 40, which is the output of the EGR term table 118. The product 160 of the exhaust gas recirculation ratio 24 (EGR) of the engine at the current operating state and the EGR term coefficient 110 used to calculate the exhaust gas recirculation portion 44 of the soot ratio 40 is added, generally indicated by box 162, to the functional timing value 112 ($f_{EGR}$) of the exhaust gas recirculation ratio 24, to define an EGR portion sum 164. The EGR portion sum 164 is then multiplied, generally indicated by box 166, by the difference, indicated by box 168, between the exhaust gas recirculation ratio 24 (EGR) of the engine at the current operating state and the exhaust gas recirculation base ratio 114 ($EGR_{base}$) used to calculate the exhaust gas recirculation portion 44 of the soot ratio 40, to calculate the exhaust gas recirculation portion 44 (EGRpor) of the current soot output 18.

The fuel injection pressure portion 46 (InjPpor) is calculated from Equation 7:

$$InjPpor=[(a_{InjP})(AFR)+(f_{InjP})][(InjP)-(InjP_{base})]; \qquad 7)$$

wherein AFR is the air/fuel ratio 22 of the engine at the current operating state, InjP is the fuel injection pressure 28 of the engine at the current operating state, $a_{InjP}$ is an InjP term coefficient 170 for the air/fuel ratio 22, $f_{InjP}$ is a functional timing value 172 of the fuel injection pressure 28 of the engine, and $InjP_{base}$ is a fuel injection pressure base value 174 of the engine when the engine is operating at the reference state.

The InjP term coefficient 170 for the air/fuel ratio 22 is a function of the rotational speed 30 of the engine and the fueling rate 32 of the engine. The InjP term coefficient 170 is a constant for any given combination of the rotational speed 30 and the fueling rate 32 of the engine. The InjP term coefficient 170 is determined from test data generated for each combination of the rotational speed 30 and the fueling rate 32 of the specific engine being used.

As shown in FIG. 1, defining and/or determining the InjP term coefficient 170 ($a_{InjP}$), generally indicated by box 176, which is used to calculate the fuel injection pressure portion 46 of the soot ratio 40, may include referencing an InjP term table 178 stored in the memory of the controller. The InjP term table 178 may be defined as a two dimensional table, that uses two input values to define an output value. The InjP term coefficient 170 used to calculate the fuel injection pressure portion 46 of the soot ratio 40 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the InjP term table 178, to look-up and/or define the value for the InjP term coefficient 170 used to calculate the fuel injection pressure portion 46 of the soot ratio 40, which is the output of the InjP term table 178.

The fuel injection pressure base value 174 ($InjP_{base}$) is the fuel injection pressure 28 of the engine when the engine is operating at the reference state. As shown in FIG. 1, defining and/or determining fuel injection pressure base value 174 ($InjP_{base}$), generally indicated by box 180, which is used to calculate the fuel injection pressure portion 46 of the soot ratio 40, may include referencing a InjP base table 182 stored in the memory of the controller. The InjP base table 182 may be defined as a two dimensional table, that uses two input values to define an output value. The fuel injection pressure base value 174 used to calculate the fuel injection pressure portion 46 of the soot ratio 40 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the InjP base table 182, to look-up and/or define the value for the fuel injection pressure base value 174 used to calculate the fuel injection pressure portion 46 of the soot ratio 40, which is the output of the InjP base table 182.

The functional timing value 172 ($f_{InjP}$) of the fuel injection pressure 28 is determined based upon the rotational speed 30 of the engine at the current operating state, the fueling rate 32 of the engine at the current operating state, and the fuel injection timing 26 of the engine at the current operating state. The functional timing value 172 of the fuel injection pressure 28 is determined or calculated from Equation 8)

$$f_{InjP} = b_2(f((b_1)(InjT))) + b_3; \qquad 8)$$

wherein $b_1$ is a coefficient 184 for the functional timing value 172 of the fuel injection pressure 28, $b_2$ is a coefficient 186 of the fuel injection timing 26 of the engine, $b_3$ is an adjustment value 188 of the functional timing value 172 of the fuel injection pressure 28, and InjT is the fuel injection timing 26 of the engine at the current operating state of the engine.

The functional timing value 172 ($f_{InjP}$) of the fuel injection pressure 28 is determined and/or calculated from the coefficient 184 for the functional timing value 172 of the fuel injection pressure 28, the coefficient 186 of the fuel injection timing 26 of the engine, and the adjustment value 188 of the functional timing value 172 of the fuel injection pressure 28.

Figure 4:
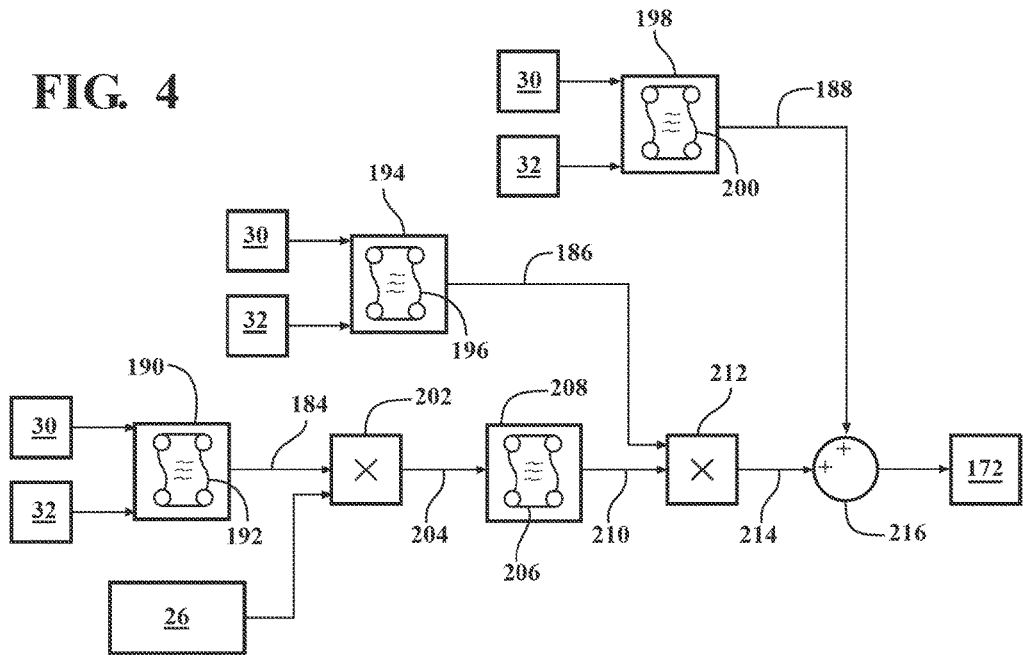
FIG. 4 is a schematic diagram showing a mapping structure for determining a functional timing value of a fuel injection pressure of the engine.

Referring to FIG. 4, the coefficient 184 ($b_1$) for the functional timing value 172 of the fuel injection pressure 28 is determined and/or defined, generally indicated by box 190, by referencing an InjP-B1 input table 192 stored in the memory of the controller. The InjP-B1 input table 192 may be defined as a two dimensional table, that uses two input values to define an output value. The coefficient 184 ($b_1$) for the functional timing value 172 of the fuel injection pressure 28 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the InjP-B1 input table 192, to look-up and/or define the value for the coefficient 184 ($b_1$) for the functional timing value 172 of the fuel injection pressure 28, which is the output of the InjP-B1 input table 192.

The coefficient 184 is a function of the rotational speed 30 of the engine and the fueling rate 32 of the engine. The coefficient 184 is a constant for any given combination of the rotational speed 30 and the fueling rate 32 of the engine. The coefficient 184 is determined from test data generated for each combination of the rotational speed 30 and the fueling rate 32 of the specific engine being used.

As shown in FIG. 4, the coefficient 186 ($b_2$) for the functional timing value 172 of the fuel injection pressure 28 is determined and/or defined, generally indicated by box 194, by referencing an InjP-B2 multiplier table 196 stored in the memory of the controller. The InjP-B2 multiplier table 196 may be defined as a two dimensional table, that uses two input values to define an output value. The coefficient 186 ($b_2$) for the functional timing value 172 of the fuel injection pressure 28 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the InjP-B2 multiplier table 196, to look-up and/or define the value for the coefficient 186 ($b_2$) for the functional timing value 172 of the fuel injection pressure 28, which is the output of the InjP-B2 multiplier table 196.

The coefficient 186 is a function of the rotational speed 30 of the engine and the fueling rate 32 of the engine. The coefficient 186 is a constant for any given combination of the rotational speed 30 and the fueling rate 32 of the engine. The coefficient 186 is determined from test data generated for each combination of the rotational speed 30 and the fueling rate 32 of the specific engine being used.

As shown in FIG. 4, the adjustment value 188 ($b_3$) for the functional timing value 172 of the fuel injection pressure 28 is determined and/or defined, generally indicated by box 198, by referencing an InjP-B3 adjustment table 200 stored in the memory of the controller. The InjP-B3 adjustment table 200 may be defined as a two dimensional table, that uses two input values to define an output value. The adjustment value 188 ($b_3$) for the functional timing value 172 of the fuel injection pressure 28 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the InjP-B3 adjustment table 200, to look-up and/or define the value for the adjustment value 188 ($b_3$) for the functional timing value 172 of the fuel injection pressure 28, which is the output of the InjP-B3 adjustment table 200.

The adjustment value 188 is a function of the rotational speed 30 of the engine and the fueling rate 32 of the engine. The adjustment value 188 is a constant for any given combination of the rotational speed 30 and the fueling rate 32 of the engine. The adjustment value 188 is determined from test data generated for each combination of the rotational speed 30 and the fueling rate 32 of the specific engine being used.

As shown in FIG. 4, the fuel injection timing 26 (InjT) of the engine at the current operating state is multiplied, generally indicated by box 202, by the coefficient 184 ($b_1$) for the functional timing value 172 of the fuel injection pressure 28, which is the output of the InjP-B1 input table 192. The product 204 of the fuel injection timing 26 and the coefficient 184 ($b_1$) for the functional timing value 172 of the fuel injection pressure 28 is used as an input into an InjP calibration table 206. The InjP calibration table 206 is a one dimensional table that uses a single input to define a single output value. Accordingly, the output value of the InjP calibration table 206 defines the value of the function $f((b_1)(InjT))$. As such, the function $f((b_1)(InjT))$ is determined, generally indicated by box 208, from the InjP calibration table 206 based upon the product 204 of the coefficient 184 ($b_1$) for the functional timing value 172 of the fuel injection pressure 28 and the fuel injection timing 26 of the engine at the current operating state. Accordingly, the controller may use the product 204 of the coefficient 184 ($b_1$) for the functional timing value 172 of the fuel injection pressure 28 and the fuel injection timing 26 of the engine at the current operating state as the single input into the InjP calibration table 206, to look-up and/or define the value for the function $f((b_1)(InjT))$, which is the output 210 of the InjP calibration table 206.

The InjP calibration table 206 is universal for the rotational speed 30 and the fuel rate 32 of the engine. The InjP calibration table 206 is developed by adjusting the values of the table 206 to achieve the best soot rate estimation at all engine speeds and fueling rate conditions.

As shown in FIG. 4, the value for the function $f((b_1)(InjT))$, which is the output 210 of the InjP calibration table 206, is multiplied, generally indicated by box 212, by the value for the coefficient 186 ($b_2$) for the functional timing value 172 of the fuel injection pressure 28, which is the output of the InjP-B2 multiplier table 196. The product 214 of the function $f((b_1)(InjT))$ and the coefficient 186 ($b_2$) for the functional timing value 172 of the fuel injection pressure 28 is then added, generally indicated by box 216, to the adjustment value 188 ($b_3$) for the functional timing value 172 of the fuel injection pressure 28, which is the output of the InjP-B3 adjustment table 200, to define and/or calculate the functional timing value 172 ($f_{InjP}$) of the fuel injection pressure 28.

Referring back to FIG. 1, the air/fuel ratio 22 (AFR) of the engine at the current operating state is multiplied, generally indicated by box 218, by the InjP term coefficient 170 used to calculate the fuel injection pressure portion 46 of the soot ratio 40, which is the output of the InjP term table 178. The product 220 of the air/fuel ratio 22 (AFR) of the engine at the current operating and the InjP term coefficient 170 used to calculate the fuel injection pressure portion 46 of the soot ratio 40 is added, generally indicated by box 222, to the functional timing value 172 ($f_{InjP}$) of the fuel injection pressure 28, to define an InjP portion sum 224. The InjP portion sum 224 is then multiplied, generally indicated by box 226, by the difference, generally indicated by box 228, between the fuel injection pressure 28 (InjP) of the engine at the current operating state and the fuel injection pressure base value 174 ($InjP_{base}$) used to calculate the fuel injection pressure portion 46 of the soot ratio 40, to calculate the fuel injection pressure portion 46 (InjPpor) of the current soot output 18.

The fuel injection timing portion 48 (InjTpor) is calculated from Equation 9:

$$InjTpor = (f_{InjT})[(InjT) - (InjT_{base})]; \qquad 9)$$

wherein InjT is the fuel injection timing 26 of the engine at the current operating state, $f_{InjT}$ is a functional timing value 230 of the fuel injection timing 26 of the engine, and $InjT_{base}$ is a fuel injection timing base value 232 of the engine when the engine is operating at the reference state.

The fuel injection timing base value 232 ($InjT_{base}$) is the fuel injection timing 26 of the engine when the engine is operating at the reference state. As shown in FIG. 1, defining and/or determining the fuel injection timing base value 232 ($InjT_{base}$) generally indicated by box 234, which is used to calculate the fuel injection timing portion 48 of the soot ratio 40, may include referencing an InjT base table 236 stored in the memory of the controller. The InjT base table 236 may be defined as a two dimensional table, that uses two input values to define an output value. The fuel injection timing base value 232 used to calculate the fuel injection timing portion 48 of the soot ratio 40 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the InjT base table 236, to look-up and/or define the value for the fuel injection timing base value 232 used to calculate the fuel injection timing portion 48 of the soot ratio 40, which is the output of the InjT base table 236.

The functional timing value 230 ($f_{InjT}$) of the fuel injection timing 26 is determined based upon the rotational speed 30 of the engine at the current operating state, the fueling rate 32 of the engine at the current operating state, and the fuel injection timing 26 of the engine at the current operating state. The functional timing value 230 of the fuel injection timing 26 is determined or calculated from Equation 10)

$$f_{InjT} = b_2(f((b_1)(InjT))) + b_3; \qquad 10)$$

wherein $b_1$ is a coefficient 238 for the functional timing value 230 of the fuel injection timing 26, $b_2$ is a coefficient 240 of the fuel injection timing 26 of the engine, $b_3$ is an adjustment value 242 of the functional timing value 230 of the fuel injection timing 26, and InjT is the fuel injection timing 26 of the engine at the current operating state of the engine.

The functional timing value 230 ($f_{InjT}$) of the fuel injection timing 26 is determined and/or calculated from the coefficient 238 for the functional timing value 230 of the fuel injection timing 26, the coefficient 240 of the fuel injection timing 26 of the engine, and the adjustment value 242 of the functional timing value 230 of the fuel injection timing 26.

Figure 5:
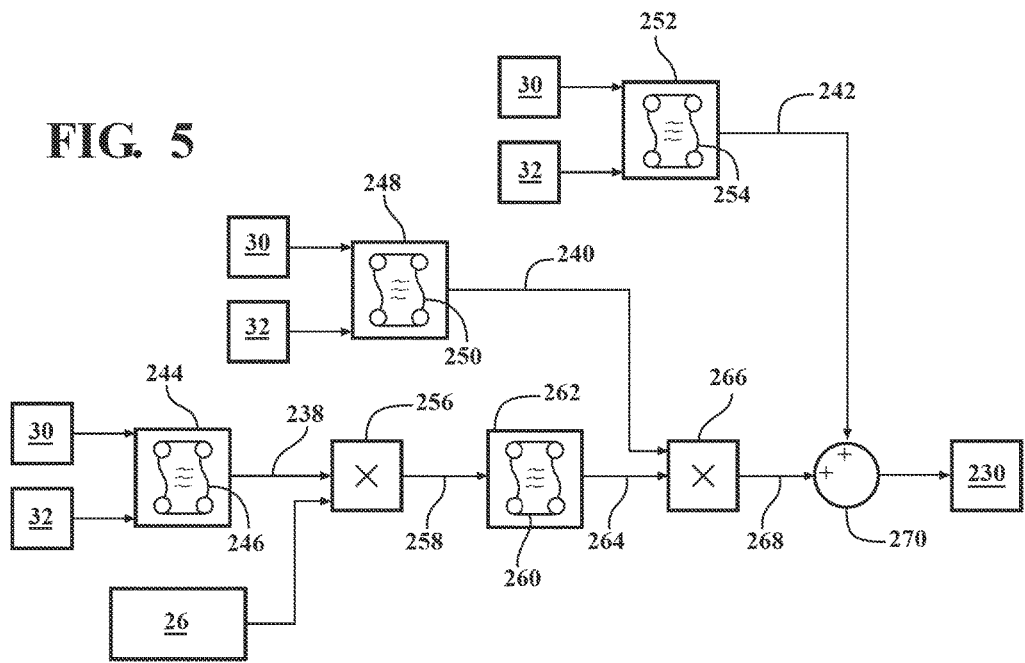
FIG. 5 is a schematic diagram showing a mapping structure for determining a functional timing value of a fuel injection timing of the engine.

Referring to FIG. 5, the coefficient 238 ($b_1$) for the functional timing value 230 of the fuel injection timing 26 is determined and/or defined, generally indicated by box 244, by referencing an InjT-B1 input table 246 stored in the memory of the controller. The InjT-B1 input table 246 may be defined as a two dimensional table, that uses two input values to define an output value. The coefficient 238 ($b_1$) for the functional timing value 230 of the fuel injection timing 26 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the InjT-B1 input table 246, to look-up and/or define the value for the coefficient 238 ($b_1$) for the functional timing value 230 of the fuel injection timing 26, which is the output of the InjT-B1 input table 246.

The coefficient 238 is a function of the rotational speed 30 of the engine and the fueling rate 32 of the engine. The coefficient 238 is a constant for any given combination of the rotational speed 30 and the fueling rate 32 of the engine. The coefficient 238 is determined from test data generated for each combination of the rotational speed 30 and the fueling rate 32 of the specific engine being used.

As shown in FIG. 5, the coefficient 240 ($b_2$) for the functional timing value 230 of the fuel injection timing 26 is determined and/or defined, generally indicated by box 248, by referencing an InjT-B2 multiplier table 250 stored in the memory of the controller. The InjT-B2 multiplier table 250 may be defined as a two dimensional table, that uses two input values to define an output value. The coefficient 240 ($b_2$) for the functional timing value 230 of the fuel injection timing 26 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the InjT-B2 multiplier table 250, to look-up and/or define the value for the coefficient 240 ($b_2$) for the functional timing value 230 of the fuel injection timing 26, which is the output of the InjT-B2 multiplier table 250.

The coefficient 240 is a function of the rotational speed 30 of the engine and the fueling rate 32 of the engine. The coefficient 240 is a constant for any given combination of the rotational speed 30 and the fueling rate 32 of the engine. The coefficient 240 is determined from test data generated for each combination of the rotational speed 30 and the fueling rate 32 of the specific engine being used.

As shown in FIG. 5, the adjustment value 242 ($b_3$) for the functional timing value 230 of the fuel injection timing 26 is determined and/or defined, generally indicated by box 252, by referencing an InjT-B3 adjustment table 254 stored in the memory of the controller. The InjT-B3 adjustment table 254 may be defined as a two dimensional table, that uses two input values to define an output value. The adjustment value 242 ($b_3$) for the functional timing value 230 of the fuel injection timing 26 is based upon the rotational speed 30 of the engine and the fueling rate 32 of the engine at the current operating state. Accordingly, the controller may use the rotational speed 30 of the engine and the fueling rate 32 of the engine at the current operating state as the two inputs into the InjT-B3 adjustment table 254, to look-up and/or define the value for the adjustment value 242 ($b_3$) for the functional timing value 230 of the fuel injection timing 26, which is the output of the InjT-B3 adjustment table 254.

The adjustment value 242 is a function of the rotational speed 30 of the engine and the fueling rate 32 of the engine. The adjustment value 242 is a constant for any given combination of the rotational speed 30 and the fueling rate 32 of the engine. The adjustment value 242 is determined from test data generated for each combination of the rotational speed 30 and the fueling rate 32 of the specific engine being used.

As shown in FIG. 5, the fuel injection timing 26 (InjT) of the engine at the current operating state is multiplied, generally indicated by box 256, by the coefficient 238 ($b_1$) for the functional timing value 230 of the fuel injection timing 26, which is the output of the InjT-B1 input table 246. The product 258 of the fuel injection timing 26 and the coefficient 238 ($b_1$) for the functional timing value 230 of the fuel injection timing 26 is used as an input into an InjT calibration table 260. The InjT calibration table 260 is a one dimensional table that uses a single input to define a single output value. Accordingly, the output value of the InjT calibration table 260 defines the value of the function $f((b_1)(InjT))$. As such, the function $f((b_1)(InjT))$ is determined, generally indicated by box 262, from the InjT calibration table 260 based upon the product 258 of the coefficient 238 ($b_1$) for the functional timing value 230 of the fuel injection timing 26, and the fuel injection timing 26 of the engine at the current operating state. Accordingly, the controller may use the product 258 of the coefficient 238 ($b_1$) for the functional timing value 230 of the fuel injection timing 26 and the fuel injection timing 26 of the engine at the current operating state as the single input into the InjT calibration table 260, to look-up and/or define the value for the function $f((b_1)(InjT))$, which is the output 264 of the InjT calibration table 260.

The InjT calibration table 260 is universal for the rotational speed 30 and the fuel rate 32 of the engine. The InjT calibration table 260 is developed by adjusting the values of the table 260 to achieve the best soot rate estimation at all engine speeds and fueling rate conditions.

As shown in FIG. 5, the value for the function $f((b_1)(InjT))$, which is the output 264 of the InjT calibration table 260, is multiplied, generally indicated by box 266, by the value for the coefficient 240 ($b_2$) for the functional timing value 230 of the fuel injection timing 26, which is the output of the InjT-B2 multiplier table 250. The product 268 of the function $f((b_1)(InjT))$ and the coefficient 240 ($b_2$) for the functional timing value 230 of the fuel injection timing 26 is then added, generally indicated by box 270, to the adjustment value 242 ($b_3$) for the functional timing value 230 of the fuel injection timing 26, which is the output of the InjT-B3 adjustment table 254, to define and/or calculate the functional timing value 230 ($f_{InjT}$) of the fuel injection timing 26.

Referring back to FIG. 1, the functional timing value 230 ($f_{InjT}$) of the fuel injection timing 26 is multiplied, generally indicated by box 272, by the difference, generally indicated by box 274, between the fuel injection timing 26 (InjT) of the engine at the current operating state and the fuel injection timing base value 232 ($InjTj_{base}$) used to calculate the fuel injection timing portion 48 of the soot ratio 40, to calculate the fuel injection timing portion 48 (InjTpor) of the current soot output 18.

As noted above, the soot ratio 40 of the engine is calculated from Equation 2:

$$\text{sootratio} = e^{((AFRpor)+(EGRpor)+(InjPpor)+(InjTpor))}. \qquad 2)$$

Accordingly, referring to FIG. 1, the air/fuel ratio portion 42 (AFRpor) of the soot ratio 40, the exhaust gas recirculation portion 44 (EGRpor) of the soot ratio 40, the fuel injection pressure portion 46 (InjPpor) of the soot ratio 40, and the fuel injection timing portion 48 (InjTpor) of the soot ratio 40 are added together, generally indicated by box 276, to define the exponent 278 of the exponential function ($e^x$). The exponential function may then be calculated, generally indicated by box 280 to define the soot ratio 40.

As noted above, the estimated value of the current soot output 18 of the engine is calculated from Equation 1:

$$\text{sootoutput} = (M_{exh})(\text{Soot}_{base})(\text{sootratio}); \qquad 1)$$

Accordingly, referring to FIG. 1, the soot output base rate 34 of the engine, the soot ratio 40, and the mass flow rate 20 of the exhaust gas are multiplied together, generally indicated by box 282, to define or calculate the estimated value of the current soot output 18 of the engine.

The detailed description and the drawings or figures are supportive and descriptive of the invention, but the scope of the invention is defined solely by the claims. While some of the best modes and other embodiments for carrying out the claimed invention have been described in detail, various alternative designs and embodiments exist for practicing the invention defined in the appended claims.

The invention claimed is:

1. A method of estimating a current soot output from an engine, the method comprising:

sensing a mass flow rate of a flow of exhaust gas from the engine;

defining a soot output base rate of the engine, with a controller, when the engine is operating at a reference state;

calculating a soot ratio for a current operating state of the engine, with a controller;

multiplying the mass flow rate, the soot output base rate, and the soot ratio together to define an estimated value of the current soot output from the engine; and controlling an exhaust gas treatment system connected to the engine, with the controller, based upon the estimated value of the current soot output from the engine;

wherein the soot ratio is calculated from the equation:

$$\text{sootratio} = e^{((AFRpor)+(EGRpor)+(InjPpor)+(InjTpor))};$$

wherein AFRpor is an air/fuel ratio portion of the soot ratio, EGRpor is an exhaust gas recirculation portion of the soot ratio, InjPpor is a fuel injection pressure portion of the soot ratio, and InjTpor is a fuel injection timing portion of the soot ratio;

wherein the air/fuel ratio portion is calculated from the equation:

$$\text{AFRpor} = [(a_{AFR})(AFR) + (f_{AFR})][AFR - (AFR_{base})];$$

wherein AFR is an air/fuel ratio of the engine at the current operating state, $a_{AFR}$ is an AFR term coefficient for the air/fuel ratio, $f_{AFR}$ is a functional timing value of the air/fuel ratio, and $AFR_{base}$ is an air/fuel ratio base value of the engine when the engine is operating at the reference state;

wherein the exhaust gas recirculation portion is calculated from the equation:

$$\text{EGRpor} = [(a_{EGR})(EGR) + (f_{EGR})][(EFR) - (EGR_{base})];$$

wherein EGR is an exhaust gas recirculation ratio of the engine at the current operating state, $a_{EGR}$ is an EGR term coefficient for the exhaust gas recirculation ratio, $f_{EGR}$ is a functional timing value of the exhaust gas recirculation ratio, and $EGR_{base}$ is an exhaust gas recirculation base ratio of the engine when the engine is operating at the reference state;

wherein the fuel injection pressure portion is calculated from the equation:

$$\text{InjPpor} = [(a_{InjP})(AFR) + (f_{InjP})][(InjP) - (InjP_{base})];$$

wherein AFR is the air/fuel ratio of the engine at the current operating state, InjP is a fuel injection pressure of the engine at the current operating state, $a_{InjP}$ is an InjP term coefficient for the air/fuel ratio, $f_{InjP}$ is a functional timing value of the fuel injection pressure of the engine, and $InjP_{base}$ is a fuel injection pressure base value of the engine when the engine is operating at the reference state; and wherein the fuel injection timing portion is calculated from the equation:

$$\text{InjTpor} = (f_{InjT})[(InjT) - (InjT_{base})];$$

wherein InjT is a fuel injection timing of the engine at the current operating state, $f_{InjT}$ is a functional value of the fuel injection timing of the engine, and $InjT_{base}$ is a fuel injection timing base value of the engine when the engine is operating at the reference state.

2. The method set forth in claim 1 wherein defining the soot output base rate of the engine when the engine is operating at the reference state includes referencing a table to determine the soot output base rate based upon a rotational speed of the engine and a fueling rate of the engine at the current operating state.

3. The method set forth in claim 1 further comprising sensing the air/fuel ratio of the engine at the current operating state, sensing the exhaust gas recirculation ratio of the engine at the current operating state, sensing the fuel injection timing of the engine at the current operating state, sensing the fuel injection pressure of the engine at the current operating state, sensing a rotational speed of the engine at the current operating state, and sensing a fueling rate of the engine at the current operating state.

4. The method set forth in claim 3 further comprising referencing a table to determine the AFR term coefficient used to calculate the air/fuel ratio portion of the soot ratio, based upon the rotational speed of the engine at the current operating state, and the fueling rate of the engine at the current operating state.

5. The method set forth in claim 4 further comprising referencing a table to determine the air/fuel ratio base value used to calculate the air/fuel ratio portion of the soot ratio, based upon the rotational speed of the engine at the current operating state, and the fueling rate of the engine at the current operating state.

6. The method set forth in claim 5 further comprising determining the functional timing value of the air/fuel ratio based upon the rotational speed of the engine at the current operating state, the fueling rate of the engine at the current operating state, and the fuel injection timing of the engine at the current operating state.

7. The method set forth in claim 6 wherein determining the functional timing value of the air/fuel ratio includes calculating the functional timing value of the air/fuel ratio from the equation:

$$f_{AFR} = b_2(f((b_1)(InjT))) + b_3$$

wherein $b_1$ is a coefficient for the functional timing value of the air/fuel ratio determined from a table based upon the rotational speed of the engine at the current operating state, and the fueling rate of the engine at the current operating state;

wherein $b_2$ is a coefficient of the fuel injection timing of the engine determined from a table based upon the rotational speed of the engine at the current operating state, and the fueling rate of the engine at the current operating state;

wherein $b_3$ is an adjustment value of the functional timing value of the air/fuel ratio determined from a table based upon the rotational speed of the engine at the current operating state, and the fueling rate of the engine at the current operating state; and wherein $f((b_1)(InjT))$ is determined from a table based upon the product of the coefficient $b_1$ for the functional timing value of the air/fuel ratio and the fuel injection timing of the engine at the current operating state.

8. The method set forth in claim 3 further comprising referencing a table to determine the EGR term coefficient used to calculate the exhaust gas recirculation portion of the soot ratio, based upon the rotational speed of the engine at the current operating state, and the fueling rate of the engine at the current operating state.

9. The method set forth in claim 8 further comprising referencing a table to determine the exhaust gas recirculation base ratio used to calculate the exhaust gas recirculation portion of the soot ratio, based upon the rotational speed of the engine at the current operating state, and the fueling rate of the engine at the current operating state.

10. The method set forth in claim 9 further comprising determining the functional timing value of the exhaust gas recirculation ratio based upon the rotational speed of the engine at the current operating state, the fueling rate of the engine at the current operating state, and the fuel injection timing of the engine at the current operating state.

11. The method set forth in claim 10 wherein determining the functional timing value of the exhaust gas recirculation rate includes calculating the functional timing value of the exhaust gas recirculation rate from the equation:

$$f_{EGR}=b_2(f((b_1)(InjT)))+b_3$$

wherein $b_1$ is a coefficient for the functional timing value of the exhaust gas recirculation ratio determined from a table based upon the rotational speed of the engine at the current operating state, and the fueling rate of the engine at the current operating state;

wherein $b_2$ is a coefficient for the fuel injection timing of the engine determined from a table based upon the rotational speed of the engine at the current operating state, and the fueling rate of the engine at the current operating state;

wherein $b_3$ is an adjustment value of the functional timing value of the exhaust gas recirculation ratio determined from a table based upon the rotational speed of the engine at the current operating state, and the fueling rate of the engine at the current operating state; and wherein $f((b_1)(InjT))$ is determined from a table based upon the product of the coefficient $b_1$ for the functional timing value of the exhaust gas recirculation rate and the fuel injection timing of the engine at the current operating state.

12. The method set forth in claim 3 further comprising referencing a table to determine the InjP term coefficient used to calculate the fuel injection pressure portion of the soot ratio, based upon the rotational speed of the engine at the current operating state, and the fueling rate of the engine at the current operating state.

13. The method set forth in claim 12 further comprising referencing a table to determine the fuel injection pressure base value used to calculate the fuel injection pressure portion of the soot ratio, based upon the rotational speed of the engine at the current operating state, and the fueling rate of the engine at the current operating state.

14. The method set forth in claim 13 further comprising determining the functional timing value of the fuel injection pressure based upon the rotational speed of the engine at the current operating state, the fueling rate of the engine at the current operating state, and the fuel injection timing of the engine at the current operating state.

15. The method set forth in claim 14 wherein determining the functional timing value of the fuel injection pressure includes calculating the functional timing value of the fuel injection pressure from the equation:

$$f_{InjP}=b_2(f((b_1)(InjT)))+b_3$$

wherein $b_1$ is a coefficient for the functional timing value of the fuel injection pressure determined from a table based upon the rotational speed of the engine at the current operating state, and the fueling rate of the engine at the current operating state;

wherein $b_2$ is a coefficient for the fuel injection timing of the engine determined from a table based upon the rotational speed of the engine at the current operating state, and the fueling rate of the engine at the current operating state;

wherein $b_3$ is an adjustment value of the functional timing value of the fuel injection pressure determined from a table based upon the rotational speed of the engine at the current operating state, and the fueling rate of the engine at the current operating state; and wherein $f((b_1)(InjT))$ is determined from a table based upon the product of the coefficient $b_1$ for the functional timing value of the fuel injection pressure and the fuel injection timing of the engine at the current operating state.

16. The method set forth in claim 3 further comprising referencing a table to determine the fuel injection timing base value used to calculate the fuel injection timing portion of the soot ratio, based upon the rotational speed of the engine at the current operating state, and the fueling rate of the engine at the current operating state.

17. The method set forth in claim 16 further comprising determining the functional timing value of the fuel injection timing based upon the rotational speed of the engine at the current operating state, the fueling rate of the engine at the current operating state, and the fuel injection timing of the engine at the current operating state.

18. The method set forth in claim 17 wherein determining the functional timing value of the fuel injection timing includes calculating the functional timing value of the fuel injection timing from the equation:

$$f_{InjT}=b_2(f((b_1)(InjT)))+b_3$$

wherein $b_1$ is a coefficient for the functional timing value of the fuel injection timing determined from a table based upon the rotational speed of the engine at the current operating state, and the fueling rate of the engine at the current operating state;

wherein $b_2$ is a coefficient for the fuel injection timing of the engine determined from a table based upon the rotational speed of the engine at the current operating state, and the fueling rate of the engine at the current operating state;

wherein $b_3$ is an adjustment value of the functional timing value of the fuel injection timing determined from a table based upon the rotational speed of the engine at the current operating state, and the fueling rate of the engine at the current operating state; and wherein $f((b_1)(InjT))$ is determined from a table based upon the product of the coefficient $b_1$ for the functional timing value of the fuel injection timing and the fuel injection timing of the engine at the current operating state.

* * * * *